US009682159B2

(12) United States Patent
Wiebelitz

(10) Patent No.: US 9,682,159 B2
(45) Date of Patent: Jun. 20, 2017

(54) IMAGING DIAGNOSTICS BY COMBINING CONTRAST AGENTS

(71) Applicant: MIVENION GMBH, Berlin (DE)

(72) Inventor: Ulrike Wiebelitz, Berlin (DE)

(73) Assignee: nanoPET Pharma GmbH, Berlin (DE)

( * ) Notice: Subject to any disclaimer, the term of this patent is extended or adjusted under 35 U.S.C. 154(b) by 99 days.

(21) Appl. No.: 14/859,595

(22) Filed: Sep. 21, 2015

(65) Prior Publication Data
US 2016/0008496 A1 Jan. 14, 2016

Related U.S. Application Data

(62) Division of application No. 13/860,675, filed on Apr. 11, 2013, now Pat. No. 9,179,882, which is a division of application No. 12/666,205, filed as application No. PCT/EP2008/057886 on Jun. 20, 2008, now abandoned.

(30) Foreign Application Priority Data

Jun. 22, 2007 (EP) ..................................... 07110922

(51) Int. Cl.
A61K 51/04 (2006.01)
A61K 49/04 (2006.01)
A61K 49/06 (2006.01)
A61B 6/00 (2006.01)
A61K 49/10 (2006.01)
A61B 6/03 (2006.01)

(52) U.S. Cl.
CPC .......... A61K 51/0491 (2013.01); A61B 6/481 (2013.01); A61K 49/04 (2013.01); A61K 49/06 (2013.01); A61K 49/103 (2013.01); A61K 49/105 (2013.01); A61B 6/037 (2013.01)

(58) Field of Classification Search
CPC .................................................... A61K 51/04
See application file for complete search history.

(56) References Cited

U.S. PATENT DOCUMENTS

| 5,059,415 | A | 10/1991 | Neuwelt |
| 5,128,121 | A | 7/1992 | Berg et al. |
| 6,490,476 | B1 | 12/2002 | Townsend et al. |
| 6,628,982 | B1 | 9/2003 | Thomas et al. |
| 6,972,122 | B2 | 12/2005 | Haroon et al. |
| 7,482,592 | B2 | 1/2009 | Krieg et al. |
| 7,714,115 | B2 | 5/2010 | Grigg et al. |
| 7,925,330 | B2 | 4/2011 | Kalafut et al. |
| 8,073,525 | B2 | 12/2011 | Ladebeck et al. |
| 8,265,733 | B2 | 9/2012 | Maschke et al. |
| 2002/0061279 | A1* | 5/2002 | DeGrado ........... A61K 51/0406 424/1.89 |
| 2005/0113667 | A1 | 5/2005 | Schlyer et al. |
| 2006/0184124 | A1 | 8/2006 | Cowan et al. |
| 2006/0284096 | A1 | 12/2006 | Krieg et al. |
| 2007/0055127 | A1 | 3/2007 | Ladebeck et al. |
| 2007/0073139 | A1 | 3/2007 | Maschke et al. |
| 2007/0102641 | A1 | 5/2007 | Schmand et al. |
| 2007/0213662 | A1 | 9/2007 | Kalafut et al. |
| 2007/0282263 | A1 | 12/2007 | Kalafut et al. |
| 2008/0008366 | A1 | 1/2008 | Desh et al. |
| 2008/0076914 | A1 | 3/2008 | Grigg et al. |
| 2008/0146914 | A1 | 6/2008 | Polzin et al. |
| 2008/0167621 | A1 | 7/2008 | Wagner et al. |
| 2012/0016233 | A1 | 1/2012 | Kalafut et al. |

FOREIGN PATENT DOCUMENTS

| DE | 102005023906 | 11/2006 |
| DE | 102005045600 | 4/2007 |
| DE | 102005040107 | 5/2007 |
| EP | 0414700 | 3/1991 |
| WO | 2006037950 | 4/2006 |
| WO | 2006058280 | 6/2006 |
| WO | 2006124634 | 11/2006 |
| WO | 2007/008232 | 1/2007 |

OTHER PUBLICATIONS

Pichler, B. J. et al., "Performance Test of an LSO-APD detector in a7-T MRI Scanner for Simultaneous PET/MRI," The Journal of Nuclear Medicine, 2006, vol. 47, No. 4, pp. 639-647.
Siemens, "Magnetom Flash—BrainPET The Next Wave in the Evolution of Medical Imaging," 2006, Mar. 2006, pp. 21-23.
Lois, C. et al., "Effect of MR contrast agents on quantitative accuracy of PET in combined whole-body PET/MR imaging," Eur. J. Nucl. Med. Mol. Imaging, 2012, vol. 39, pp. 1756-1766.
Beyer, T. et al., "MR/PET—Hybrid Imaging for the Next Decade," Magnetom Flash, 2010, vol. 3, p. 24, right column, third passage, (Clinical prototype MR/PET).
Hirsch, F. W. et al., "PET/MR in children. Initial clinical experience in pediatric oncology using an integrated PET/MR scanner," Pediatr. Radiol., Jan. 11, 2013.
Brendle, C. B. et al., "Simultaneously Acquired MR/PET Images Compared with Sequential MR/PET and PET/CT: Alignment Quality," Radiology, 2013, vol. 268, No. 1, pp. 190-199.
Abraham, J. L. et al., "Dermal inorganic gadolinium concentrations: evidence for in vivo transmetallation and long-term persistence in nephrogenic systemic fibrosis," British Journal of Dermatology, Dec. 7, 2007, vol. 158, No. 2, pp. 273-280.
Karabulut, N. et al., "Contrast agents using in MR Imaging of the liver," Diagn Interv Radiol, 2006, pp. 22-30.
Bremerich, J. et al., "MR angiography with blood pool contrast agents," Eur Radiol, 2007, pp. 3017-3024.
Tweedle, M. F. et al., "Reaction of gadolinium chelates with endogenously available ions," Magnetic Resonance Imaging, 1991, vol. 9, pp. 409-415.

(Continued)

Primary Examiner — Michael G Hartley
Assistant Examiner — Jagadishwar Samala
(74) Attorney, Agent, or Firm — Millen White Zelano and Branigan, PC; John Sopp; Anthony Zelano

(57) ABSTRACT

The present invention relates to the use of a combination of several contrast agents having different properties with respect to imaging representation.

8 Claims, No Drawings

(56) References Cited

OTHER PUBLICATIONS

Cohade, C. et al., "Intial eExperience with Oral Contrast in PET/CT: Phantom and Clinical Studies," The Journal of Nuclear Medicine, 2003, vol. 44, No. 3, pp. 412-416.
Antoch, G. et al., "Focal Tracer Uptake: A Potential Aritifact inContrast-Enhanced Dual-Modality PET/CT Scans," The Journal of Nuclear Medicine, Oct. 2002, vol. 43, No. 10, pp. 1339-1342.
Antoch, G. et al, "To enhance or not to enhance? 18F-FDG and CT Contrast Agents in Dual-Modality 18F-FDG PET/CT," The Journal of Nuclear Medicine, 2004, vol. 45, No. 1 Supp, pp. 56S-65S.
Slates, R. B. et al., "A study of artefacst in simultaneous PET and MR imaging using a prototype MR compatible PET scanner," Phys. Med. Biol., 1999, vol. 44, pp. 2015-2027.
Marsden, P. K. et al., "Simultaeous PET and NMR" The British Journal of Radiology, 2002, vol. 75, pp. S53-S59.
Catana, C. et al., "Simultaneous Acquisition of Multi-slice PET and MR Images: Initial Results with a MR-compatible PET scanner," The Journal of Nuclear Medicine, Dec. 2006, vol. 47, No. 12.
Puls, R. et al., "Double contrast MRI of Thermally Ablated Liver Metastases," Fortschr Rontgenstr., 2003, vol. 175, pp. 1467-1470.
Vuorela, J. et al., "Distribution of Radiation in Synovectomy of the Knee with 166Ho_FHMA Using Image Fusion," Cancer Biotherapy and Radiopharmaceuticals, 2005, vol. 20, No. 3, pp. 333-337.
Iagaru, A. et al., "Breast MRI and 18F FDG PET/CT in the management of breast cancer," Annals of Nuclear Medicine, 2007, vol. 21, No. 1, pp. 33-38.
Wyss, M. T. et al., "Uptake of 18F-Fluorocholine, 18F-FET, and 18F-FDG in C6 Gliomas and Correlation with 131I-SIP(L19), a marker of Angiogenesis," The Journal of Nuclear Medicine, Apr. 2007, vol. 48, No. 4, pp. 608-614.
Bellin, M. F. et al., "Currently used non-specific extracellular MR contrast media," Eur Radio!, 2003, vol. 13, pp. 2688-2698.
European Search Report for EP13174573 dated Dec. 4, 2013.
Yamamoto, Y. et al., "3-deoxy-3'-[F-18]Fluorothymidine Positron Emission Tomography in Patients with Recurrent Glioblastoma Multiforme: Comparison with Gd-DTPA Enhanced Magnetic Resonance Imaging," Molecular Imaging and Biology, Oct. 19, 2006, vol. 8, No. 6, pp. 340-347.
Gallagher et al., "Metabolic trapping as a principle of radiopharmaceutical design: Some Factors Responsible for the Biodistribution of [18F]2-Deoxy-2-Fluoro-D-Glucose," Journal of Nuclear Medicine, 1978, vol. 19, pp. 1154-1161.
Hanneke et al., "Gadopentetate dimeglumine and FDG uptake in liver metastases of colorectal carcinoma as determined with MR imaging and PET," Radiology, Oct. 2005, vol. 237, pp. 181-188.
Pauleit et al., "O-(2-[18F]fluoroethyl)-L-tyrosine PET combined with MRI improves the diagnostics assessment of cerebral gliomas," Brain, 2005, vol. 128, No. 3, pp. 678-687.
Wahl et al., "Anatometabolic tumor imaging: fusion of FDG PET with CT or MRI to localize foci of increased activity," The Journal of Nuclear Medicine, Jul. 1993, vol. 34, No. 7, pp. 1190-1197.
Spence et al., "18F-FDG PET of Gliomas at Delayed Intervals: Improved Distinction Between Tumor and Normal Gray Matter," J. Nucl. Med., 2004, vol. 45, pp. 1653-1659.
Downer, Medical Solutions, Mar. 2007, pp. 76-79.
Andersen et al., "Approximation of arterial input curve data in MRI estimation of cerebral blood-tumour-barrier leakage: Comparison between Gd-DTPA and 99m Tc-DTPA input curves," Magnetic Resonance Imaging, 1996, vol. 14, No. 3, pp. 235-241.
Manning et al., "First-pass nuclear magnetic resonance imaging studies using Fadolinium-DTPA in patients with coronary artery disease," Journal of the American College of Cardiology, 1991, vol. 18, No. 4, pp. 959-965.
Wikipedia, Interpolation (Mathematik), article version dated Apr. 24, 2007.
Higuchi, T. et al., "Characterization of Normal and Infarcted Rat Myocardium Using a Combination of Small-Animal PET and Clinical MRI," The Journal of Nuclear Medicine, Feb. 2007, vol. 48, No. 2.
Schlemmer, H. et al., "Simultaneous MR/PET for brain imaging: First patient scans," J. Nucl. Med., 2007, vol. 48.
Heiss, W. et al., "Simultaneous functional and morphological brain imaging with an integrated MR/PET scanner," J. Cereb. Blood Flow Metab., 2007.
Raylmann, R. R. et al., "Simultaneous acquisition of magnetic resonance spectroscopy (MRS) data and positron emission tomography (PET) images with a prototype MR-compatible, small animal PET imager," Journal of Magnet Resonance, 2007, vol. 186, pp. 305-310.
Cho, Z. et al., "A hybrid PET-MRI: An integrated molecular-genetic imaging system with HRRT-PET and 7.0-T MRI," Int. J. Imaging System Technol., 2007, vol. 17, pp. 252-265.
Judenhofer, M. S. et al., "Simultaneous PET-MRI: a new approach for functional and morphological imaging," Nature Medicine, Apr. 2008, vol. 14, No. 4, pp. 459-465.
Zaidi, H. et al, "Current Trends in PET and Combined (PET/CT and PET/MR) Systems Design," Pet Clin, 2007, pp. 109-123.
Ortega-Lopez, N. et al., "Evaluation of magnetic resonance imaging and fluorine-18-2-deoxy-2-fluor-d-glucose positron emission tomography co-registration in patients with primary brain tumors," Gac. Med. Mex., 2007, vol. 143, No. 4, pp. 309-316.
English Translation of Ortega-Lopez, N. et al., "Evaluation of magnetic resonance imaging and fluorine-18-2-deoxy-2-fluor-d-glucose positron emission tomography co-registration in patients with primary brain tumors," Gac. Med. Mex., 2007, vol. 143, No. 4, pp. 309-316.
Hamm, B. et al., "Contrast-enhanced MR Imaging of Liver and Spleen: First Experience in Humans with a New Superparamagnetic Iron Oxide," J. Magn. Res. Imaging, 1994, vol. 4, No. 5, pp. 659-668.
Lehmann, T. M. et al., "Survey: Interpolation Methods in Medical Imaging Processing," Transactions on Medical Imaging, Nov. 1999, vol. 18, No. 11, pp. 1049-1075.
International Soceity for Cerbral Blood Flow and Metabolism, "Complex Heterogeneous: The Organ," Feb. 2004.
Van Laarhoven et al. Radiology, Oct. 2005, pp. 182-188.
Weinmann, H. J. et al., "P{harmacokinetics of GdDTPA/ Dimeglumine after intravenous injection into healthy volunteers," Physiological Chemistry and Physics and Medical N.M.R, 1984, vol. 16.
B.M. Gallagher, et al., Radiopharmaceuticals XXVII. 18F-Labeled 2-deoxy-2-fluoro-d-glucose as a radiopharmaceutical for measuring regiional myocardial glucose metabolism in vivo: Tissue distribution and imaging studies in amimals, J. Nucl. Med. 18, 990-996, 1977.
Written Submissions filed with new non-patent literature in the EPO in a parallel European Application No. 12199299.4 on Aug. 18, 2014.
EPO Communication dated Aug. 11, 2014 in parallel European Application No. 08774183.1.
Catana, C. et al. "Simultaneous in vivo positron emission tomography and magnetic resonance imaging" PNAS, 105 (10):3705-3710, Mar. 11, 2008.
Filippi, M. et al. "Ultra-high-field MR imaging in multiple sclerosis" Abstract, Journal of Neurology, Neurosurgery & Psychiatry, 85:60-66 (2014).
Forrest, W. "First PET/MRI brain images debut at SNM 2007" AuntMinne.com (Jun. 15, 2007).
Judenhofer, et al. "PET/MR Images Acquired with a Compact MR-compatible PET Dectector in a 7-T Magnet" Radiology, 244(3):807-814, (Sep. 2007).
Mainardi, L.T. et al. "A method for dynamic subtraction MR imaging of the liver" BMC Medical Imaging, 6(5):1-9 (2006).
Margolis, N. E. et al. "Initial experience: combination of MR pharmacokinetic modeling and FDG uptake using simultaneous dynamic contrast enhanced MRI and PET imaging" Proc. Intl. Soc. Mag. Reson. Med. 22, 2014, 1090.
Platzek, I. et al. "PET/MRI in head and neck cancer: initial experience" Eur J Nucl Med Mol Imaging, 40:6-11, (2013).

(56) References Cited

OTHER PUBLICATIONS

Rauscher, I. et al. "PET/MR Imaging in the Detection and Characterization of Pulmonary Lesions: Technical and Diagnostic Evaluation in Comparison to PET/CT" The Journal of Nuclear Medicine, 55(5):724-729, (May 2014).
Savio, S. et al. "Estimation of sufficient signal to noise ratio for texture analysis of magnetic resonance images" Proc of SPIE vol. 7962 79622C02.
GE Healthcare Response to Proprietors Statement of Mar. 3, 2014 from OPPO 02 in EP 2170405 B1: Mivenion GmbH Opposition. Filed in the European Patent Office on Aug. 4, 2014. EP Application No. EP08774183.1.

* cited by examiner

IMAGING DIAGNOSTICS BY COMBINING CONTRAST AGENTS

The present invention relates to the use of a combination of several contrast agents having different imaging properties.

Chronic diseases are an important field of application for imaging diagnostics. The two most frequent chronic diseases, cardiovascular diseases and tumour diseases, alone account for the greater part of the 800 million imaging diagnoses which are carried out every year worldwide. The majority of examinations are ultrasonic examinations, X-ray examinations, such as CT and MRI examinations, but also nucleomedical and optical methods are often used. For all of these examination methods, contrast agents are clinically available. Contrast agents provide specific information determined by their pharmacokinetic and pharmacodynamic properties. However, imaging examination alone often allows only for little diagnostic information. Due to this reason, it is often necessary to carry out various examinations with the same modality and different contrast agents or to carry out different examinations with different modalities, in order to allow a reliable diagnosis. This procedure involves high costs and strain/stress for the patient. Furthermore, this approach is time-consuming and, the beginning of a necessary therapy is often delayed due to the fact that several diagnostic examinations are required. A further disadvantage is the assignment of diagnostic signals from different imaging examinations. Very often, it is not possible to correlate suspect lesions of one examination to the lesions detected in another examination, which considerably complicates the diagnosis for the physician. The necessity to carry out different diagnostic examinations in order to establish a reliable diagnosis can be illustrated by the imaging diagnostics of tumours, particularly the imaging diagnostics of breast cancer.

Breast cancer is one of the most frequent tumours and the most frequent tumour disease with women. Improved early diagnosis, such as screening mammogram, and complex treatment protocols allowed a decrease in mortality over the last years. Nonetheless, a great number of breast cancer cases are only detected at a late stage. Hence, the early diagnosis of tumours is a great challenge. This is particularly important as the growth of small tumours is limited to the organ so that there is hope to remove the tumour completely and to conserve the organ if tumours are detected in early stages. Medical methods available up to present meet this requirement only inadequately. Hence, it is important to provide improved methods of early and reliable diagnosis.

Today, the physician can use various diagnostic methods with the imaging techniques playing a major role. Among the imaging techniques, ultrasonic diagnosis, CT, MRI and nucleomedical techniques, such as PET and SPECT, are the most relevant techniques. With unclear diagnostic findings, the aim is to take tissue samples from suspect lesions and to prepare and assess these samples histopathologically.

MRI examination of the female breast has very high sensitivity in comparison to other imaging modalities. Due to this modality, it is possible to detect different forms of breast cancer at an early stage. A particular advantage of MRI is the fact that imaging examination is not complicated in a significant way by non-tumerous tissue alterations, such as e.g. surgical cicatrices, tissue alterations by radiological treatment, prostheses or mastopathically altered glandular tissue. Due to these characteristics, MRI has meanwhile found a large range of applications.

The high sensitivity of MRI of the breast is, however, associated with low specificity. Low specificity implies that almost all malignant tumours are detected but that, at the same time, many foci which, in the course of subsequent examinations, are found to be harmless, are represented as malignant tumours. The reason for this is that MRI uses contrast agents which improve the method to a degree that allows to show even minor irregularities in the breast tissue to be examined. These contrast agents are not appropriate to make a satisfactory distinction between benign and malignant lesions. As a consequence of the diagnostic results, the physician has to initiate further examinations which are to assess the presumptive diagnostic findings in greater detail. On the one hand, further imaging methods are applied, on the other hand, it is possible to make an MRI-based biopsy of the suspect tissue and establish an exact diagnosis by histological examination. The fact that this is a method of high technical standard involving high costs is one of the reasons why MRI imaging has not yet been established as standard method for breast cancer diagnosis. As to clinical application of CT, the situation is similar. CT also plays a major role in tumour diagnosis. For example, the CT-contrast agent Ultravist® is used for imaging CT diagnosis of liver tumours. This method also shows minor specificity with respect to the contrast agents based diagnosis. Thus, it is a central task to improve the specificity of diagnostic imaging in order to make it widely applicable.

One possibility to improve the specificity of information provided by an imaging modality is to use improved signal altering or signal modulating contrast agents. Today, contrast agents are clinically available for most of the imaging methods. These contrast agents are selected in such a way that, on the one hand, their application is acceptable with humans and that, on the other hand, they can interact with the physical signal of the relevant examination modality in a very specific manner. Most empirical data regarding the application of contrast agents relate to X-ray-based CT examination methods. Diagnostic radiology uses contrast agents which attenuate the X-rays. These are, amongst others, substances with a great number of elements having high electron density, such as iodine. These contrast agents can be applied in a variety of ways in humans, however, the most frequent applications are applications in which the contrast agents are introduced by bolus injection into the blood circulation. By applying contrast agents in this way, it is possible to make the blood flow in a specific organ visible for the duration of the examination. This application form of contrast agents allows to obtain important information on the anatomy, morphology and function of specific organs. Thus, it is possible to obtain information on the condition of a blood vessel by detecting a contrast agent in this blood vessel and by visualizing the vessel lumen. Existing constrictions of the coronary arteries can be made visible by coronary angiography without difficulties, thus, leading to the diagnosis of coronary stenosis. Another parameter providing significant diagnostic data is the velocity with which the contrast agent applied flows into the organ. Thus, it is possible to draw conclusions with respect to the blood circulation within a particular organ. The application of contrast agents is as important in MRI as it is in radiodiagnostics. For X-ray-based examinations as well as for MRI examinations, a great number of different contrast agents is available to the physician. However, all of these contrast agents are optimised for specific application purposes. Extracellular contrast agents (ECCM) play a major role in the detection of tissue lesions, such as tumours, diseases of the central nervous system (CNS) and diseases of the cardio-vascular system. These contrast agents are optimised in such a way that their concentration in the blood is rapidly reduced from a maximum concentration to a minimum concentration within very few minutes after their application (alpha slope, blood kinetics). Furthermore, they are characterised in that they have plasma protein binding of less than 90%, preferably of less than 70%. ECCM can easily be selected from a series of different contrast agents by in-vivo imaging studies in animals or human. In these in-vivo studies a fast decline of the imaging signal over the target lesion or reference regions indicates a characteristic of ECCM. Due to their small molecular size and the incomplete binding to plasma proteins, they easily pass the capillary barrier. Another significant property of the ECCM is the lack of interaction with biological structures. ECCM do not bind to specific structures in the lesion to be examined and are not altered by these structures. Due to these properties, they can pass the capillary barriers in both directions and, thus, they are capable of demarcating suspect lesions from the surrounding healthy tissue. This process is known as extravasation and occurs also in an intact capillary system, though with clearly reduced velocity. In particular with tumour diseases, diseases of the central nervous system and diseases of the cardio-vascular system, the capillary barrier is defect and ECCM leakage occurs preferably at these sites. Extravasation of the ECCM results in a signal increase in the lesion in comparison to the healthy surroundings. Within the first minutes after injection of an ECCM, signal increases of up to 100% can be observed. This first phase of the extravasation process is also known as wash-in. This phase can be followed by a rapid but often incomplete washout phase. The signal in the lesions can be inferior to the signal in the surroundings, as, due to the disturbed barrier function, the wash-out process in the lesion can occur faster than in the healthy tissue where the intact barrier reduces the velocity of back flow. Back flow is however always caused by fast decrease of the ECCM concentration in the blood. This is a characteristic property of the ECCM used according to the invention. Fast elimination from blood circulation requires incomplete and loose binding of plasma protein and is ensured by renal and/or hepatic elimination capacity, in contrast to ECCM, lesion-specific contrast agents (LSCM) used according to the invention are characterised in that they can interact with a specific target structure in the organism or are altered by said specific structures in such a way that they can be visualised in by an imaging technique as a consequence of the interaction or alteration. A further property by which they can be distinguished from ECCM is their longer retention in blood circulation. This property can be achieved, for example, by ensuring that the relevant LSCM are characterised by a stronger plasma protein binding of more than 90%. The characteristic properties of LSCM can easily be detected by in-vivo imaging studies in animals or human. A continuous accumulation in the target lesion indicates a LSCM.

The most important ECCM in MRI is gadolinium-DTPA (Gd-DTPA). Gd-DTPA is a paramagnetic substance which leads to a reduction of the T1 relaxation time of the surrounding tissue. It is a substance with low molecular weight, which does not interact with structures of the organism and is not altered by these. Due to this property, it is capable of leaving the capillary system even if the capillary barrier is intact and vascular permeability is normal. Having left the capillary system, Gd-DTPA spreads in the extravasal space. Many diseases, such as e.g. tumour diseases, inflammatory organ alterations or tissue injuries due to apoplexia result in damage of the capillary barrier. If patients suffering form such diseases are subjected to MRI examinations with the contrast agent Gd-DTPA, the contrast agent extravasates to an increased degree in areas where the capillary barrier is damaged. The concentration in the tissue is increased particularly in these areas, which is noticeable by an increased signal in the MRI image. This effect is followed by an increased back diffusion also known as wash-out phenomenon. This characteristic behaviour, which is also known as "wash-in/wash-out" phenomenon, can be used in MRI diagnosis in various ways, e.g. for the detection of tumours with high scanning speeds during the injection of contrast agent in MRI. In particular the imaging diagnostics of suspect tissue alterations of the female breast proved that the "wash-in/wash-out" phenomenon allows to detect probably all malignant breast lesions above a certain size. The method, however, also has a great disadvantage. In addition to the existing malignant tumours, many benign foci are detected. These are various benign tissue alterations of different kinds which bear no risk for the patients.

So far, no method is known which would enhance the specificity of highly sensitive imaging methods in a satisfactory way.

A possibility to enhance the specificity of imaging examination methods consists in carrying out different contrast agent-based examinations. In the literature, methods are known wherein the suspect disease lesions were characterised by subsequently using two different MRI contrast agents. For this monomodal method, the examination was carried out in two steps. First, an LSCM was applied. Due to the long retention period, the concentration of an ECGM could only be examined by a delayed second examination. This approach has the decisive disadvantage that by carrying out the examinations separately, an overlap of the two signals is possible only in a limited way. Thus, the method known from literature loses some of its sensitivity and specificity and offers no advantage [Marcarini L. et. al; Radiol. Med. (2006) 111: 1087-1102].

Surprisingly, it was found that the use of ECCM in combination with at least one further imaging contrast agent or signalling substance which tends to concentrate specifically in the disease lesion (lesion-specific contrast agent/LSCM) is a completely new imaging method having a markedly higher specificity than the application of an ECCM alone. The combination of the invention is characterised in that the ECCM and the LSCM are applied at the same time or the LSCM is applied with a short time delay of 30 minutes maximum, preferably of 20 minutes maximum, most preferably of 10 minutes maximum after the application of the ECCM. Thus, the method of the invention allows to interpolate the different imaging signals and to achieve a lesion diagnosis of high sensitivity and high specificity. Interpolation means that, in a given examination area/region, at least two signals differing from each other can be/are related in space and in time. Thus, the invention resolves the disadvantages of the state of the art—with diagnostic methods being carried out independently from one another—by combining ECCM and LSCM which allows a useful interpolation of the different imaging signals. Diagnostic methods being carried out independently from one another means, that the patient is moved from the examination table in between the diagnostic methods. The ECCM is used to detect the lesions, whereas the LSCM is used to characterise the lesions. By using this method, the number of false positive diagnostic findings can be decreased significantly and physician as well as patient can be spared unnecessary examinations. Unexpectedly, the present invention provides for an increased diagnosis sensitivity and specificity in comparison with the state of the art, wherein images from independent examinations are merely spatially overlaid. The present invention furthermore allows for adjusting examination parameters such as the spatial area which lies within the focus of the diagnostic apparatus or the irradiation intensity as a consequence to the result obtained by one of the contrast agents, thereby enhancing the result obtained with the other contrast agent. Used in combination according to the invention, ECCM and LSCM are contrast agents with complementary action properties.

Thus, subject matter of the present invention is an extracellular contrast agent (ECCM) for the diagnosis of lesions in combination/conjunction with a lesion-specific contrast agent (LSCM). According to the invention, the individual contrast agents of the combination of ECCM and LSCM may be imaging contrast agents for a single synthetic imaging method (monomodal) or multiple synthetic imaging methods (polymodal).

The combination of ECCM and LSCM according to the invention envisages a fixed time sequence for the application of the individual substances. In the case of the monomodal technique, the ECCM is administered first and the LSCM is administered subsequently. The LSCM is administered at the earliest when the ECCM level in the blood has reached a level that allows detecting the LSCM.

Thus, subject matter of the present invention is also an extracellular contrast agent (ECCM) for the diagnosis of lesions, wherein, in the case of the monomodal technique, the ECCM is provided for in a manner suited for the intended use for administration as first contrast agent and the LSCM is provided for in a manner suited for the intended use as second contrast agent to be administered after the ECCM level in the blood has declined to a level that allows the detection of the ECCM. In the case of the polymodal technique, the contrast agents may be provided for in a manner suited for the intended use in such a way that they can be administered at the same point in time. In the case of the polymodal technique, they may, however, be provided for in a manner suited for the intended use in such a way that the LSCM is prepared for administration as first contrast agent and the ECCM for administration as second contrast agent. This approach surprisingly provides the possibility to investigate the distribution of the disease in the whole body as the first step, and to perform detailed characterisation of the suspicious lesions with ECCM as the second step.

Preferably, in a polymodal technique, the LSCM is administered as first contrast agent and the ECCM is administered as second contrast agent, where the image registration of the LSCM is performed first, and the image registration for the ECCM is performed second. As an example, in the combination of 18F-Fluordeoxyglucose (FDG) as LSCM for PET imaging with Ultravist® as ECCM for CT imaging for a combined PET/CT imaging of cancer, after administration of FDG and subsequent administration of Ultravist®, the PET exam with image registration of the LSCM is performed. As FDG is accumulated not only in e.g. cancer cells, but also in a variety of normal cells (e.g. brain) and cells affected by other disease (e.g. inflammation), the subsequent CT imaging for image registration of the ECCM is performed only in the regions with increased FDG uptake to allow a high-resolution imaging with a slice collimation of 2 mm or less, preferably of 1 mm or less in CT for detection of subtle morphologic signs, e.g. of cancer.

Preferably, the combination of the invention is, however, used in such a way that the ECCM is administered first in order to detect suspect lesions in the relevant organs. The LSCM is then used in order to provide information with respect to the kind of lesions based on its concentration in said lesions.

In the case of the polymodal technique, both contrast agents can be administered sequentially—like in the monomodal technique—and simultaneously. Thus, subject matter of the present invention is an extracellular contrast agent (ECCM) for the diagnosis of lesions in combination with LSCM, wherein in the case of the polymodal method
   either the ECCM is prepared for administration as first contrast agent and the LSCM is prepared as second contrast agent to be administered after the level of ECCM in the blood has declined to a level that allows the detection of the ECCM, or
   the ECCM and the LSCM are prepared for simultaneous administration.

The contrast agents may also be prepared in such a way that the LSCM is prepared for administration as first contrast agent and the ECCM for administration as second contrast agent. Subject matter of the present invention is also a method for the diagnosis of lesions, wherein an extracellular contrast agent (ECCM) is administered in combination/conjunction with a lesion-specific contrast agent (LSCM) and, preferably, the imaging signals are interpolated immediately.

The ECCM of the invention are signaling and signal-modulating substances for synthetic imaging techniques which, after having been applied to humans, rapidly reach a high peak concentration in the blood due to the bolus-like injection which is normally used and the high concentration of said ECCM rapidly declines from this high level by their spreading into the whole organism (alpha slope, elimination kinetics). In general, this process is terminated within 5 to 10 minutes after application. In general, after 5 to 10 minutes after application the substance levels in circulation are below a level allowing imaging detection. Renal and hepatitic elimination, or a combination of both, is decisive for further clearance of substance levels from the circulation. For fast elimination from blood circulation, the imaging substances must be of small molecular size. The elimination of substances with a molecular weight of more than 2,000 to 5,000 is significantly slower compared to the elimination of substances with a molecular weight of up to 1,000 g/mol. Hence, the ECCM of the invention have a molecule size of less than 2,000 g/mol, preferably of less than 1,000 g/mol. Another important property of the ECCM is their hydrophilicity. Substances having high hydrophilicity are eliminated fast. The elimination of substances having low hydrophilicity is significantly delayed. Hydrophilicity of the EGCM of the invention is characterised by a distribution coefficient of log P<−2 (less than minus two in n-butanol/water), preferably by a distribution coefficient of log P<−3 (less than minus three in butanol/water).

ECCM of the invention are contrast agents for MRI, X-ray-based techniques such as CT, optical techniques, optoacoustical techniques, ultrasonic techniques and nucleomedical techniques. They are characterised in that they do not interact with structures of the organism after injection and in that they are not altered in their signalling property by interaction with structures of the organism. Their movement is determined by the velocity of distribution and elimination. After reaching the maximum concentration in the blood, the process of distribution is completed and substance levels which are no longer sufficient for imaging are reached preferably after 10 minutes. Hence, 30 minutes after injection at the latest, preferably 20 minutes after injection, most preferably after 10 minutes after injection, the concentration of the contrast agents of the invention in the blood circulation is reduced to a degree that the LSCM can be applied.

ECCM are particularly preferred which exhibit a blood concentration that is reduced to a level allowing administration of the LSCM after 30 minutes at the latest, particularly preferred after 10 to 15 minutes. Animal imaging studies can be applied to discriminate between ECCM and LSCM. A fast decline of the imaging signal over the target lesion or reference region is a characteristic of ECCM, whereas LSCM exhibits a continuous accumulation in the target lesion over more than 30 to 60 min after application.

Thus, in the present invention, the ECCM and LSCM are defined by their different target lesion elimination times. Hereby, the absolute elimination time of each contrast agent from the target lesion is not of particular significance, but rather the relative elimination times of the contrast agents to be used as ECCM/LSCM pair. This means that the ECCM is eliminated in 20% of the time or less, more preferably in 10% of the time or less, with respect to the elimination time from the target lesion of the LSCM, wherein preferably, the time difference between the elimination of the ECCM and the LSCM to a level of 10% of the maximum concentration of ECCM and LSCM in the target lesion is at least 20 min, more preferably at least 30 minutes. Consequently, many contrast agents may be used both as LSCM or ECCM, depending whether the second contrast agent which is used in conjunction therewith has a slower or more rapid elimination. Hereby, the tissue type which is comprised by the area of interest will have to be accounted for, as several contrast agents show different elimination times in different tissue types. In general, a person skilled in the art will recognize combinations of contrast agents which represent appropriate ECCM/LSCM pairs for a given application and a given tissue type, as the elimination behaviour of most contrast agents has already been described in great detail. In some cases however, a simple experiment will have to be conducted in which the elimination behaviour of a contrast agent in a certain tissue type is monitored. The skilled person, such as a radiologist, is trained to carry out such experiments routinely. In this context, the term "eliminated" or "elimination" means that the level of contrast agent in a given area of diagnostic interest has reached a value of 10% or less of the maximum level after injection.

ECCM are substances, contrast agents or effector molecules, preferably selected from the group comprising:
  metal complexes with paramagnetic metals,
  superparamagnetic, ferromagnetic or ferrimagnetic iron oxide particles with polymeric protective coating,
  complex-bound, chelator-bound and covalently bound radioactive nuclides,
  gas-filled, polymeric microparticles or microvesicles,— gas precursors,
  organic, metallo-organic or anorganic chromophores or fluorophores,
  structures which biosynthetically form organic chromophores or fluorophores,
  structures with a high absorption cross section for X-rays,
  structures having an effect on electric impedance.

Subject matter of the invention is the use of ECCM containing paramagnetic metal ions. Preferred paramagnetic metal ions are ions of transitional metals and lanthanoid metals (e.g. metals having the atomic numbers 6-9, 21-29, 42, 43, 44, or 57-71), in particular ions of Cr, V, Mn, Fe, Co, Ni, Cu, La, Ce1 Pr, Nd, Pm, Sm, Eu, Gd, Tb, Dy, Ho, Er, Tm, Yb and Lu. Mn, Cr, Fe, Gd and Dy are preferred. Gd is particularly preferred.

These ions are stably bound or complexed by complex forming structures or groups of chelators. The latter are macro-cyclic or open-chain polyaminocarboxylic acids. Macro-cyclic chelator groups are preferably tetraazacyclododecane chelators, such as 1,4,7,10-tetraazacyclododecane-N,N',N'',N'''-tetraacetic acid (DOTA); 1,4,7,10-tetraazacyclododecane-N,N',N''-triacetic acid (DO3A); 1-Oxa-4,7,10-triazacyciododecane-N,N',N''-tretraacetic acid (OTTA); trans(1,2)-cyclohexanodiethylentriamine pentaacetic acid (CDTPA) and analogues thereof, or ethylenamine chelator groups, such as N,N,N',N'',N''-diethylenetriamine pentaacetic acid (DTPA), ethyleneediamine tetraacetic acid (EDTA), as well as their chemical substitution derivatives at the ethylene and/or acetic acid residues. Further derivatives are DTPA-BMA, DPDP, TMT and HPDO3A, gadubotrol (Gadovist®), gadopentetatic acid/dimeglumine salt (Magnevist®), gadobenic acid (Multihance®), gadodiamide (Omniscan), gadoxetic acid/disodium salt (Primovist®; Gd-EOB-DTPA), and gadoteridol (Prohance®).

Gadubotrol (Gadovist®), gadopentetatic acid/dimeglumine salt (Magnevist®), gadobenic acid (Multihance®), gadodiamide (Omniscan), gadoxetic acid/disodium salt (Primovist®; Gd-EOB-DTPA), and gadoteridol (Prohance®) are particularly preferred.

Subject matter of the invention are ECCM containing superparamagnetic iron oxide particles. These are biocompatible and acceptable due to the stabilizing protective coating. The iron oxide particles with protective coating have a diameter of 20-500 nm, preferably of 20-200 nm. Protective coatings consists of polymers, in particular polysaccharides such as dextran. SPIOs, USPIOs, MIONs are particularly preferred.

Subject matter of the invention are ECCM containing chromophores or fluorophores. Chromophores or fluorophores are structures which have an extended system of delocalized electrons, which absorb and fluoresce within a spectral range of 300-1400 nm. Chromophores or fluorophores with an absorption and/or emission maximum of 400-600 nm (visible fluorescence) as well as an absorption and/or emission maximum of 650-1000 nm, in particular 700-900 nm (near-infrared fluorescence).

Chromophores or fluorophores with visible fluorescence are NBD, fluoresceins, rhodamines, tetrapyrroles (e.g. porphyrines, protoporphyrine SX), pyrilium dyes, Thai pyrilium dyes, croconium dyes, squarylium dyes, benzophenoxazinium dyes, benzothiaphenothiazinium dyes, anthraquinones, naphthoquinones, phthaloylacridones, azo dyes, diazo dyes and complexes of the lanthanoid metals La, Ce, Pr, Nd1 Pm, Sm, Eu, Gd, Tb, Dy, Ho, Er, Tm, Yb, and Lu, Eu, Tb, Yb with macrocyclic or open-chain polyaminocarboxylic acids or polyaminocarboxylic acids phosphoric acids. Fluorescein is particularly preferred.

Chromophores or fluorophores with near-infrared fluorescence are polymethin dyes, particularly cyanine dyes, merocyanines, phthalocyanines, naphthalocyanines, triphenylmethines, croconium dyes, squary[upsilon]urn dyes. Indocyanines, in particular indocyanine green, DODCI1 DTDCI, DOTCI and DDTCI and derivatives are preferred. Indocyanine green (ICG, CardioGreen, IC Green, DiagnoGreen) is particularly preferred.

Examples can be found in "Topics in Applied Chemistry: Infrared absorbing dyes" Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals" Haugland, Molecular Probes Inc, 1996, DE-A-4445065, DE-A-4326466, JP-A-3/228046, Narayanan et al., J. Org. Chem. 60: 2391-2395 (1995), Lipowska et al., Heterocyclic Comm. 1: 427-430 (1995), Fabian et al., Chem. Rev. 92: 1197 (1992), WO96/23525, Strekowska et al., J. Org. Chem. 57: 4578-4580 (1992), WO (Axis) and WO96/17628.

Subject matter of the invention are also ECCM comprising particulate or vesicular polymers which contain, transport and/or release air or fluorinated gases (e.g. SFe or perfluorinated alkanes with 1-6 C-atoms or other gases as described in WO97/29783). Echovist®, Levovist, Sonavist®, Sonuvue and Optison® are particularly appropriate.

Subject matter of the invention are ECCM containing radionuclides. Radionuclides are non-metal nuclides as well as metal nuclides for the techniques of SPECT (single photon emission computed tomography) or PET (positron emission tomography), respectively.

Non-metal nuclides are covalently bound to carbons of chemical structures. A particularly preferred non-metal nuclide is radioactive iodine (SPECT: $^{125}$I, $^{123}$I, $^{131}$I, PET: $^{124}$I) or carbon $^{11}$C (PET).

Metal radionuclides are preferably $^{90}$Y, $^{99m}$Tc, $^{111}$Sn, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb and $^{141}$Ce (for SPECT) and $^{86}$Y, $^{94m}$Tc, $^{110m}$In, $^{68}$Ga, $^{64}$Cu (for PET). These are bound by complex forming structures or radioactive chelators.

Chelators for metal radionuclides are structures with donor atoms, such as N, S, O, which bind the metals in appropriate configuration in space and form a cyclical metal complex or chelates. These are in particular ISI3S, N2S2 systems on the basis of aminoalkyl, thioalkyl, aminocarbonyl, thiocarbonyl structure elements (Kirk-Othmer Encyclopedia of Chemical Technology, Vol. 5, 339-368).

Chelators on the basis of N3S and N2S2 are described e.g. in U.S. Pat. Nos. 4,444,690; 4,670,545; 4,673,562; 4,897,255; 4,965,392; 4,980,147; 4,988,496; 5,021,556 and 5,075,099, WO92/08494. Furthermore, representative chelators are described in U.S. Pat. No. 5,559,214 A, WO 95/26754, WO 94/08624, WO 94/09056, WO 94/29333, WO 94/08624, WO 94/08629 A1, WO 94/13327 A1 and WO 94/12216 A1; WO89/00557, U.S. Pat. Nos. 4,647,447; 5,367,080; 5,364,613. Chelates are also modified proteins which bind e.g. $^{99m}$Tc (U.S. Pat. No. 5,078,985).

Chelate structures are selected from mycrocyclic or open-chain amino carboxylic acids. Macrocyclic chelator groups are preferably tetraazacyclododecane chelators, such as 1,4,7,10-Tetraazacyciododecane-N,N',N'',N'''-tetraacetic acid (DOTA); 1,4,7,10-tetraazacyclododecane-N, N',N''-triacetic acid (DO3A); 1-Oxa-4,7,10-triazacyclododecane-N,N',N''-triacetic acid (OTTA) and dibenzo[18]crown-6, $(CH_3)_6$-[14]-4,11]-dien-$N_4$, and (2.2.2-cryptate). Open-chain amino carboxylic acids are, for example, trans(1,2)-cyclohexano-diethylentriamine pentaacetic acid (CDTPA) and analogues thereof, N,N,N',N'',N''-diethylenetriamine pentaacetic acid (DTPA), ethylene diamine tetraacetic acid (EDTA), N-(2-hydroxy)-ethylene-diamine triacetic acid, nitrilotriacetic acid, N,N-Di-(2-hydroxyethyl)glycine, ethylenebis-(hydroxyphenylglycine) and derivatives thereof by chemical substitution at the ethylene and/or acetic acid residues. Further derivatives are DTPA-BMA, DPDP, TMT and HPDO3A.

Moreover, chelate structures are selected from the substance classes of polyphosphates, such as sodium polyphosphate and hexametaphosphoric acid; 1,3-diketones, e.g. acetylacetone, trifluoracetylacetone, thenoyltrifluoroacetone; hydroxycarboxy[upsilon]c acids, e.g. lactic acid, citric acid, gluconic acid and 5-sulfosalicylic acid, polyamines, e.g. ethylenediamine, diethylenetriamine, triethylenetetraamine, triaminotriethylamine; amino alcohols, e.g. triethanolamine and N-{2-hydroxyethyl)-ethylenediamine; aromatic heterocyclic bases, e.g. 2,2'-diimidazole, picolinamine, dipicolinamine, 1,10-phenanthrolin; phenols, e.g. salicylaldehyde, disulfopyrocatechol; aminophenois, e.g. 8-hydroxyquinoline oximesuifonic acid; oximes, e.g. dimethylglyoxime, salicylaldoxime; peptides with chelating end groups, e.g. polycystein, polyhistidine, polyasparaginic acid, polyglutamine acid, glycine-glycine-cystein or combinations of such amino acids; Schiff's bases, e.g. disalicyl-aldehyde, 1,2-propylendiimine; tetrapyrroles, e.g. porphyrins, tetraphenylporphyrins, benzoporphyrins, chlorines, tetraphenylchlorines, benzochlorines, bacteriochlorines, pheophorbides; purpurinimides, expanded tetra- and pentapyrroles (texaphyrines); sulphur compounds, e.g. toluene-dithiole, meso-2,3-dimercaptosuccinic acid, dimercaptopropanol, thioglycolic acid, sodium diethyldithiocarbamate, dithizone, diethyldithiophosphoric acid, thiourea; phosphonic acids, e.g. nitrilotrimethylene phophonic acid, ethylene diamine-tetra(methylene phosphonic acid), hydroxyethylidendiphosphonic acid or combinations of 2 or more of the structures mentioned.

Complex forming substances for $^{99m}$Tc are, furthermore, $^{99m}$Tc(I)(H$_2$O)$_3$(CO)$_3^+$, from which the $^{99m}$Tc-tricarbonyl complex with amino carboxylic acids or other chelating donor atoms is formed.

Subject matter of the invention are ECCM which exhibit X-ray absorption, in particular triiodized aromatic hydrocarbons and complexes with lanthanoid ions La, Ce, Pr, Nd, Pm1 Sm, Eu, Gd, Tb, Dy, Ho, Er, Tm, Yb, and Lu, Eu, Tb, Yb, preferably Gd, Tb, Dy, Ho, and structures containing triiodized aromatic hydrocarbons and complexes with tanthanoid ions and iodixanol (Visipaque®), iopromid (Ultravist®), ioxaglinic acid (Hexabrix®), iomeprol (Imeron®), iopamidol, iotrolan (Isovist), iosurcal (Melitrast), iohexol (Omnipaque®), amidotrizoic acid (Peritrast), meglumine ioxithalamate (Telebrix), iobitridol (Xenetix®) and gadolinium-DTPA. Iodixanol (Visipaque®), iopromid (Ultravist®), ioxaglinic acid (Hexabrix®), iomeprol (Imeron®), iopamidoi, iotrolan (Isovist), iosurcal (Melitrast), iohexol (Omnipaque®), amidotrizoic acid (Peritrast), meglumine ioxithalamate (Telebrix), iobitridol (Xenetix®), and gadolinium-DTPA are preferred.

In a particularly preferred embodiment, the ECCM is gadolinium DTPA.

The lesion-specific contrast agents (LSCM) according to the invention are signalling or signal-modulating substances for image synthesis procedures characterised in that they interact with structures in the organism or they are modified by structures in the organism as to their signalling properties and they provide additional imaging information which improve the specificity of the method. Said additional information can be information as to anatomy, morphology, function, metabolism or molecular expression of specific factors. The substances according to the invention are characterised in that after application in the lesion tissue they concentrate continuously and, in contrast to ECCM, remain in the lesion over a longer period of time during examination and do not exhibit any wash-in/wash-out phenomenon. The concentration can be achieved by different mechanisms which aim at preventing fast elimination from the blood circulation. The lesion-specific agents according to the invention can bind to specific binding sites, concentrate in cell membranes, be activated by enzyme activity, bind to extracellular proteins, absorbed by cells of the RES or enter cells of the lesion tissue. These substances are characterised in that their elimination from the blood circulation takes clearly more time in comparison to the ECCM. Due to said longer period of time, the agents are capable of accumulating in the suspect lesions by the mechanisms mentioned and stay there. Preferably after 15 minutes to 24 hours, particularly preferred after 15 minutes to 3 hours, the process leads to demarcation of the disease lesion from the surrounding healthy tissue, which can be diagnostically measured. With this demarcation which can be measured diagnostically, it is of no importance whether the LSCM concentrates in the tissue of the disease lesion or in the surrounding healthy tissue.

Preferably, the LSCM accumulates in the lesion after 10 minutes and stays there for at least one hour, whereas particularly preferred the concentration of the LSCM in the lesion continuously increases within the period of 10 minutes to 60 minutes.

LSCM according to the invention are contrasting agents for the MRI1 for X-ray-based techniques such as e.g. CT1 for optical techniques, for optoacoustic techniques, for ultrasonic techniques and for nuclear medicine techniques.

The LSCM are active substances, contrasting agents or effector molecules, selected from the following group, comprising:
  metal complexes with paramagnetic metals,
  superparamagnetic, ferromagnetic or ferrimagnetic iron oxide particles with polymeric protective coatings,
  complex-bound, chelator-bound and covalently bound radionuclides,
  gas-filled, polymeric microparticles or -vesicles,
  gas precursors,
  organic, metal-organic or inorganic chromophores and fluorophores,
  structures biosynthetically forming organic chromophores or fluorophores,
  structures with high absorption cross section for X-rays,
  structures influencing electric impedance.

Use of LSCM containing paramagnetic metal ions are subject matter of the invention. Preferred paramagnetic metal ions are ions of the transmission and lanthanoid metals (e.g. metals of atom numbers 6-9, 21-29, 42, 43, 44, or 57-71), in particular ions of Cr, V, Mn, Fe, Co, Ni, Cu, La, Ce, Pr, Nd, Pm, Sm, Eu, Gd, Tb, Dy, Ho, Er, Tm, Yb and Lu. Mn, Cr, Fe, Gd and Dy are preferred. Gd is particularly preferred.

These ions are stably bound or complexed by complex forming structures or chelator groups. The latter are polyaminocarboxylic acids with macrocyclic or open-chain structure. Groups of macrocyclic chelator agents are preferably tetraazacyclododecane chelates, such as 1,4,7,10-tetraazacyclododecane-N,N',N'',N'''-tetraacetic acid (DOTA); 1,4,7,10-tetraazacyclododecan-N,N',N''-triacetic acid (DO3A); 1-Oxa-4,7,10-triazacyclododecane-N,N',N''-triacetic acid (OTTA); trans(1,2)-cyclohexanodiethylentriamine pentaacetic acid (CDTPA) and analogues thereof, or ethylenamine chelator groups, such as N,N,N',N'',N'''-diethylenetriamine pentaacetic acid (DTPA), ethylenediamine tetraacetic acid (EDTA), as well as their derivatives by chemical substitution at the ethylene and/or acetic acid residues. Further derivatives are DTPA-BMA, DPDP, TMT and HPDO3A.

Gadofosveset (Vasovist®), Gadofluorine, Gadofluorine-M and Gadomer-17 are particularly preferred.

LSCM containing superparamagnetic iron oxide particles are subject matter of the invention. These are biocompatible and acceptable due to their stabilising protective coatings. Specifically, the iron oxide particles with protective coating have a diameter of 20 to 500 nm, preferably 20-200 nm. Protective coatings consist of polymers, in particular polysaccharides such as dextran.

SPIOs, USPIOs1 MIONs, Ferucarbutran (Resovist®, Supravist®) are particularly preferred.

LSCM containing chromophores or fluorophores are subject matter of the invention. Chromophores or fluorophores are structures with an elaborate system of delocalised electrons, which absorb and fluoresce within the spectral region of 300 to 1400 nm. Chromophores or fluorophores with an absorption and/or emission maximum of 400 to 600 nm {visible fluorescence) as well as an absorption and/or emission maximum of 650 to 1000 nm, in particular 700 to 900 nm (near-infrared fluorescence) are preferred.

Chromophores or fluorophores with visible fluorescence are NBD1 Fluorescein, rhodamines, tetrapyrroles (e.g. porphyrins, protoporphyrin IX)1 pyrilium dyes, thaipyrilium dyes, croconium dyes, squarilium dyes, benzophenoxazinium dyes, benzothiaphenothiazinium dyes, anthraquinones, napthoquinones, phthaloylacridones, azo dyes, diazo dyes, as well as complexes of the lanthanoide metals La, Ce, Pr, Nd, Pm, Sm, Eu, Gd, Tb, Dy, Ho, Er, Tm, Yb, and Lu1 Eu1 Tb, Yb with macrocyclic or open-chain polyaminocarboxylic acid or polyaminocarboxylic acids phosphoric acids.

Chromophores or fluorophores with near-infrared fluorescence are polymethin dyes, in particular cyanin dyes, merocyanins, phthalocyanins, naphthalocyanins, triphenylmethins, croconium dyes, squarilium dyes. Examples can be found in "Topics in Applied Chemistry: Infrared absorbing dyes", Ed. M. Matsuoka, Plenum, N.Y. 1990, "Topics in Applied Chemistry: The Chemistry and Application of Dyes", Waring et al., Plenum, N.Y., 1990, "Handbook of Fluorescent Probes and Research Chemicals", Haugland, Molecular Probes Inc, 1996, DE-A-4445065, DE-A-4326466, JP-A-3/228046, Narayanan et al., J. Org. Chem. 60: 2391-2395 (1995), Lipowska et al., Heterocyclic Comm. 1: 427-430 (1995), Fabian et al., Chem. Rev. 92: 1197 (1992), WO96/23525, Strekowska et al., J. Org. Chem. 57: 4578-4580 (1992), WO (Axis) and WO96/17628, Chromophores with targeting properties are preferred. Targeting properties of chromophores can be achieved by conjugation of chromophores to targeting molecules such as peptides, antibodies or other synthetic proteins.

The use of active substances biosynthentically forming chromophores or fluorophores after administration of the active substances is subject matter of the invention. 5-aminolaevulin acid (5-ALA) and ester of 5-ALA are mentioned to be preferred.

LSCM consisting of particulate or vesicular polymers containing, transporting and releasing air or fluorinated gases (e.g. SF6 or perfluorinated alkanes with 1-6 atoms or other gases as described in WO97/29783) are subject matter of the invention. Particulate polymers coupled to target-searching peptides or protein are particularly preferred.

LSCM containing radionuclides are subject matter of the invention. Radionuclides are both non-metal nuclides and metal nuclides, each for SPECT (single photon emission computed tomography) or PET (positron emission tomography) technique.

Non-metal nuclides are covalently bound to carbons of chemical structures. A particularly preferred non-metal nuclide is radioactive iodine (SPECT: $^{125}$I, $^{123}$I, $^{131}$I; PET: $^{124}$I) or carbon $^{11}$C (PET).

Metal radionuclides are preferably $^{90}$Y, $^{99m}$Tc, $^{111}$In, $^{47}$Sc, $^{67}$Ga, $^{51}$Cr, $^{177m}$Sn, $^{67}$Cu, $^{167}$Tm, $^{97}$Ru, $^{188}$Re, $^{177}$Lu, $^{199}$Au, $^{203}$Pb and $^{141}$Ce (for SPECT) and $^{86}$Y, $^{94m}$Tc, $^{110m}$In, $^{68}$Ga, $^{64}$Cu (for PET). These are bound by complex forming substances or radiochelators.

Chelators for metal nuclides are structures with donor atoms such as N, S, O, which bind metals in an appropriate spatial arrangement and form a cyclic metal complex or chelates. These are, in particular, $N^3S$, $N_2S_2$ systems on the basis of aminoalkyl, thioalkyl, aminocarbonyl, thiocarbonyl structure elements (Kirk-Othmer Encyclopedia of Chemical Technology, Vol. 5, 339-368).

Chelates on the basis of $N_3S$ and $N_2S_2$ are described, for example, in U.S. Pat. Nos. 4,444,690; 4,670,545; 4,673,562; 4,897,255; 4,965,392; 4,980,147; 4,988,496; 5 5,021,556 and 5,075,099, WO92/08494. Representative chelators are further described in U.S. Pat. No. 5,559,214 A, WO 95/26754, WO 94/08624, WO 94/09056, WO 94/29333, WO 94/08624, WO 94/08629 A1, WO 94/13327 A1 and WO 94/12216 A1; WO89/00557, U.S. Pat. Nos. 4,647,447; 5,367,080; 5,364,613. Chelates are also modified proteins binding e.g. $^{99m}$Tc (U.S. Pat. No. 5,078,985).

Chelate structures are selected from macrocyclic or openchain aminocarboxylic acids. Macrocyclic chelator groups are preferably tetraazacyclododecane chelates, such as 1,4,7,10-tetraazacyclododecane-N,N',N'',N'''-tetraacetic acid (DOTA); 1,4,7,10-tetraazacyclododecan-N,N'N''-triacetic-acid (DO3A); 1-Oxa-4,7,10-triazacyclododecane-N,N',N''-triacetic acid (OTTA) as well as dibenzo[18]crown-6, $(CH_3)_6$-[14]-4,11]-dien-N4, and (2.2.2-cryptate). Openchain amino carboxylic acids are, for example, trans(1,2)-cyclohexano-diethylentriamine pentaacetic acid (CDTPA) and analogues thereof, N,N,N',N'',N''-diethylenetriamine pentaacetic acid (DTPA), ethylenediamine tetraacetic acid (EDTA), N-(2-hydroxy)-ethylenediamine triacetic acid, nitrilo triacetic acid, N,N-di-(2-hydroxyethyl)-glycine, ethylenebis-(hydroxyphenylglycine) as well as their derivatives by chemical substitution at the ethylene and/or acetic acid residues. Further derivatives are DTPA-BMA, DPDP, TMT and HPDO3A.

Furthermore, chelate structures are selected from the substance classes of the polyphosphates, such as e.g. sodiumtripolyphosphate and hexametaphosphoric acid; 1,3-diketones, e.g. acetyl acetone, trifluoracetyl acetone, thenoyltrifluoracetone; hydroxy carbonic acid, e.g. lactic acid, citric acid, gluconic acid, and 5-sufosalicyl acid; polyamines, e.g. ethylenediamine, diethylentriamine, triethylentetraamine, triaminotriethylamine; aminoalcohols, e.g. triethanolamine and N-(2-hydroxyethyl)-ethylendiamine; aromatic heterocyclic bases, e.g. 2,2'-diimidazol, picolinamine, dipicolinamine, 1,10-phenanthrolin; phenols, e.g. salicylaldehyde, disulfopyrocatechol; aminophenoles, e.g. 8-hydroxychinolin oxime sulfonic acid; oximes, e.g. dimethylglyoxime, salicylaldoxime; peptide with chelating end groups, e.g. polycystein, polyhistidine, polyasparagine acid, polyglutamine acid, glycine-glycine-cysteine, or combinations of amino acids of that kind; Schiff's bases, e.g. disalicylaldehyde, 1,2-Propylendiime; tetra pyrrole, e.g. porphyrins, tetraphenylporphyrines, benzoporphyrins, chlorines, tetraphenylchlorins, benzochlorins, bacteriochlorins, pheophorbides; purpurinimides, expanded tetra- and pentapyrroles (texaphyrins); sulphur compounds, e.g. toluendithiol, Meto-2,3-dimercaptosuccinic acid, dimercaptopropanol, sodium diethyldithiocarbamate, dithizone, diethyldithiophosphoric acid, thiourea; phosphonic acids, e.g., nitrilotrimethylenphosphonic acid), ethylenediaminetetra(methylenephosphonic acid), hydroxyethyliden diphosphonic acid, or combinations of 2 or more of the structures mentioned.

Complex forming structures for $^{99m}$Tc are furthermore $^{99m}Tc(I)(H_2O)_3(CO)_3^+$ from which the $^{99m}$Tc tricarbonyl complex with amino carbonic acids or other chelating donor atoms is formed.

Chelator structures and complex forming substances are bound to carrier, vector, targeting or transporter molecules such as e.g. polymers, proteins, peptides, antibodies, oligonucleotides, polysaccharides and combinations and derivatives thereof, via linkers. In this context, chelator structures and complex forming substances are linked by means of functional groups of the chelator backbone, by means of derivatisation of donor groups into derivatised donor groups such as e.g. acids into amides, alcohols into ethers, thioles into thioethers, or by means of free coordination sites of the metal. The coupling to carrier, vector, targeting or transporter molecules can take place in molar ratios of 1 to 100. Linker and derivatives for chelators are described in WO94/08629, WO94/09056, WO96/20754.

Preferred structures are $^{99m}$Tc-Medronat, $^{9am}$Tc-Sestamibi, $^{99m}$Tc-ECD, $^{99m}$Tc-MAG3, $^{111}$In-DTPY-octreotide, $^{111}$In-DTPA-octreotate, $^{18}$F-fluordesoxyglucose (FDG), $^{18}$F-dopamine, $^{18}$F-L-DOPA, $^{18}$F-fluorcholine, $^{18}$F-fluormethylethylcholin, $^{18}$F-fluordihydro-testosterone, $^{68}$Ga-NODA-GATOC, $^{68}$Ga-DOTYTOC.

LSCM exhibiting an absorption of X-rays are subject matter of the invention, in particular triiodated aroma substances and complexes with lanthanoid ions La, Ce, Pr, Nd, Pm, Sm, Eu1 Gcl1 Tb, Dy, Ho, Er, Tm, Yb, and Lu, Eu, Tb, Yb, preferably Gd, Tb, Dy, Ho, as well as structures containing the triiodated aroma substances and complexes with lanthanoid ions.

A particular advantage of the combination of ECCM and LSCM according to the invention is the possibility of using high-resolution imaging. With use of ECCM alone, the use of high-resolution imaging was not possible, since the measure intervals available are very short. However, the combination of ECCM and LSCM according to the invention makes it possible to use high-resolution imaging to obtain specific morphological information.

During any imaging methods, the assessment of exact morphological details depends on a high spatial resolution, in order to obtain high-resolution images, however, a longer examination period is necessary. Moreover, measuring methods have to be applied which are unsuitable for the synthetic imaging of the ECCM, since an increase of the spatial resolution leads to a significant increase of the measuring time and a reduction of the ratio of signal and noise. Furthermore, high-resolution measuring methods are unsuitable for obtaining rapid changes in the distribution of the contrast agent, as necessary for the rapid distribution of ECCM.

The individual components of the combination of ECCM and LSCM according to the invention can be imaging contrasting agents or signalling substances for synthetic imaging methods (monomodal) or multiple (polymodal, multimodal) imaging methods.

The monomodal methods can be selected from the group comprising: MRT, PET, CT, optical imaging, ultrasound, SPECT, X-ray.

Synthetic imaging methods which are appropriate for the illustration of combinations of ECCM and LSCM are fusion methods of different imaging methods such as PET-CT, PET-MRI, PET-optical imaging, MRI-$CT_1$ ultrasound optical imaging, PET-SPECT, SPECT-CT, MRT-optical imaging and SPECT-MRT.

For the use of a combination according to the invention, which is illustrated by means of polymodal methods, devices and software are used which visualise the signals of the individual components separately as to space and time and which carry out an automatic comparison of the spatial and temporal signal intensities for each suspect lesion or suspect area.

With monomodal application of the combination of the invention, first, for example, the ECCM is applied and then, following with a time delay, the LSCM is applied. The time interval between the application of the ECCM and the LSCM is determined in such a way that the application of LSCM only takes place when the blood level of ECCM has sunk to a low level and no longer interferes with the subsequent application of the LSCM. In that way, the signals of the imaging agents cannot overlap and influence each other. Since the ECCM has fallen to such low level only ten minutes after application, the subsequent application must be carried out with a delay.

In case the combination of ECCM and LSCM according to the invention are visualised by means of polymodal synthetic imaging, the ECCM and the LSCM can also be applied simultaneously or with a very small delay. By using different synthetic 15 imaging methods, overlap of the individual signalling components is avoided. The signalling components of the ECCM and the LSCM can be visualised separately. The almost simultaneous application is appropriate, above all, if radioisotopes with a short decay time are used. This applies, e.g. if $^{18}F$-based PET tracer are combined with the MRI ECCM Gd-DTPA.

Thus, the combination of ECCM and LSCM is the subject matter of the present invention when used as:
  monomodal time-delayed application, e.g. monomodal measurement 0-15 minutes after injection of the ECCM and second measurement 15 minutes to 24 hours after injection of the LSCM
  polymodal time-delayed application
  polymodal simultaneous application The time-delayed application of the individual components of the combination can be achieved by different devices. The combination according to the invention can be carried out by two-chamber or multiple-chamber syringes or cartridges. A further device for the administration of the combination according to the invention is a device for carrying out the time-controlled application of the individual components. Hereby, the time control is carried out in correspondence with the application regimen for the LSCM and ECCM as described for the method of the present invention.

Thus, subject matter of the present invention is an application device for the combined application of an extracellular contrast agent (ECCM) for the diagnosis of lesions in combination/connection with a lesion-specific contrast agent (LSCM), wherein the application device has at least two chambers or receptacles for the separate absorption and application of the ECCM and the LSCM.

Said application device can be a two-chamber or multiple-chamber syringe, it can also be a two-chamber or multiple-chamber cartridge. Furthermore, an apparatus comprising two distinct chambers containing an LSCM and an ECCM, respectively, wherein the release of contrast agent is controlled with an individual pump for each chamber, and wherein the outlets of the two chambers are fitted with tubing which is connected by a Y-piece which ends in a single tube so that both contrast agents are applied to the patient via this single tube may be used as application device.

Furthermore, an embodiment of the present invention is the use of an application device for the administration of an LSCM and an ECCM to a subject or patient, whereby the application regimen for the LSCM and ECCM is as described for the method of the present invention.

EXAMPLES

Example 1

A middle-aged patient. This patient suffered from a malignant brain tumour, a glioblastoma, and was treated for it. Apart from an operation, the treatment also included radiotherapy of the brain with increased radiation in the former operation area using directed stereotactic techniques. After about six months, the patient's initially good clinical situation deteriorated. The clinical examination results in presumed tumour growth recurring.

Diagnostic imaging by means of a PET-CT device combination can illustrate tumours both by using X-ray contrast agents and by using PET isotopes. With an extracellular CT contrast agent such as e.g. Ultravist® a region accumulating contrast agent inhomogeneously in the region of the former tumour bed can be seen. With regard to differential diagnosis, apart from a tumour recurring—a local relapse—, cell death caused by high radiation—radionecrosis—is possible.

The PET isotope $^{18}F$-fluordeoxyglucose (FDG) as LSCM, which was injected simultaneously, provides the explanation for the differential diagnosis: the missing concentration of the LSCM in the cells of the region, which, in the CT, had shown a concentration of ECCM, proves the presence of radionecrosis. Further therapy consists in the administration of corticoids; the patient's prognosis is clearly better than in the case of a local relapse being present.

Example 2

A patient, typically between 50 and 70 years of age, is admitted to hospital for further diagnosis and therapy due to blood deposits in the stool. The coloscopy carried out showed a malign tumour of the colon. During the ultrasound scan of the liver, which was also carried out, an individual, defined focus was found in the right hepatic lobe which lead to the presumption of a metastasis in the liver, a liver metastasis.

The magnetoresonance tomography which was carried out, first, with an extracellular contrast agent (EECM, e.g. Magnevist®), then directly followed by a lesion-specific contrast agent (LSCM, e.g. Resovist®), confirmed, in the first step, the presence of a liver focus in the right hepatic lobe by means of ECCM. Differentiation of the type of tumour, however, is not possible. In this case, only the accumulation of the tumour with the LSCM showed that the cells of this dimension are liver cells and not tumour cells. Thus, metastasis of the colon tumour could be excluded, the diagnosis of a benign simple hemangioma of the liver could be secured by the combined contrast agents examination. The patient is subjected to a normal tumour operation of the colon.

Example 3

A patient, typically in his late 50 s or early 60 s with a history of a recent heart attack is now being investigated for viable myocardium before cardiac bypass surgery. The patient's history includes a low grade nicotine abuse 20 years ago with overall eight pack-years exposure and a history of tuberculosis during adolescence. Previous diagnostic coronary angiography has revealed stenoses in the coronary arteries. PET imaging with use of $F^{18}$-FDG as radiotracer revealed viable myocardium with the possibility to improve cardiac function with a revascularization procedure. Coincidentally an increased tracer uptake was seen during cardiac PET imaging in the left upper lobe of the lung, being consistent with cancer or infectious disease.

A targeted contrast enhanced high-resolution thin slice computed tomography scan was performed in the upper lung lobes showing a well enhancing, approximately 2 cm measuring lesion. The high resolution thin slice images clearly showed a solid appearance of the tumor and very thin streaky structures surrounding the tumor in a radiate appearance, being typical for spiculae of a lung cancer. The combination of contrast enhancement in the solid lesion and the speculated appearance of the tumor secured the diagnosis of a small lung cancer.

The entire disclosure of all applications, patents and publications, cited herein and of corresponding application No. 07110922.7 EP, filed Jun. 22, 2007, and PCT/EP2008/057886, filed Dec. 22, 2008, are incorporated by reference herein.

The invention claimed is:

1. A polymodal method for imaging a lesion in a patient comprising:
    administering to said patient:
        an extracellular contrast medium (ECCM) selected from the group consisting of: gadobutrol, gadopentetatic acid or a salt thereof, gadobenic acid, gadodiamide, gadoxetic acid/disodium salt and gadoteridol; and
        a lesion-specific contrast medium (LSCM) selected from the group consisting of: $^{99m}$Tc-Medronat, $^{99m}$Tc-Sestamibi, $^{99m}$Tc-ECD, $^{99m}$Tc-MAG3, $^{111}$In-DTPY-octreotide, $^{111}$In-DTPA-octreotate, $^{18}$F-fluordesoxyglucose, $^{18}$F-dopamine, $^{18}$F-L-DOPA, $^{18}$F-fluorcholine, $^{18}$F-fluormethylethylcholin, $^{18}$F-fluordihydro-testosterone, $^{68}$Ga-NODAGATOC and $^{68}$Ga-DOTATOC, wherein the LSCM is enriched in the lesion 10 minutes after administration to said patient and is retained in the lesion for at least 1 hour; and
    subjecting the patient to polymodal imaging wherein at least two different imaging modalities are used to provide at least two different imaging signals which are immediately interpolated by a fusion method of the at least two different imaging modalities, wherein the at least two different imaging modalities are selected from: PET-MRI and SPECT-MRT; and
    wherein either:
        a. the ECCM and the LSCM are administered consecutively; or
        b. the ECCM and the LSCM are administered simultaneously.

2. The method of claim 1, wherein the polymodal imaging uses the combination of the imaging modalities: MRI imaging and $^{18}$F-PET tracer imaging.

3. The method of claim 1, wherein the polymodal imaging uses the combination of the imaging modalities: MRT-optical imaging and SPECT-MRT imaging.

4. The method of claim 1, wherein the ECCM and the LSCM are administered to said patient consecutively with a time delay between administrations of 10 to 30 minutes.

5. The method of claim 1, wherein the ECCM and the LSCM are administered to said patient consecutively with a time delay between administrations of 10 to 15 minutes.

6. The method of claim 1, wherein the ECCM and LSCM are administered consecutively.

7. The method of claim 1, wherein the ECCM and LSCM are administered simultaneously.

8. A kit for conducting the method of claim 1, comprising:
    an extracellular contrast medium (ECCM) selected from the group consisting of: gadobutrol, gadopentetatic acid or a salt thereof, gadobenic acid, gadodiamide, gadoxetic acid/disodium salt and gadoteridol; and
    a lesion-specific contrast medium (LSCM) selected from the group consisting of: $^{99m}$Tc-Medronat, $^{99m}$Tc-Sestamibi, $^{99m}$Tc-ECD, $^{99m}$Tc-MAG3, $^{111}$In-DTPY-octreotide, $^{111}$In-DTPA-octreotate, $^{18}$F-fluordesoxyglucose, $^{18}$F-dopamine, $^{18}$F-L-DOPA, $^{18}$F-fluorcholine, $^{18}$F-fluormethylethylcholin, $^{18}$F-fluordihydro-testosterone, $^{68}$Ga-NODAGATOC and $^{68}$Ga-DOTATOC, which LSCM is enriched in the lesion 10 minutes after administration to said patient and is retained in the lesion for at least 1 hour;
wherein the kit is provided in a form suitable for simultaneous or consecutive administration of the ECCM and the LSCM to said patient.

* * * * *